US005136049A

United States Patent [19]

Hanack et al.

[11] Patent Number: 5,136,049

[45] Date of Patent: Aug. 4, 1992

[54] HETEROARYLENEMETHINES AND POLYMERS PREPARED THEREFROM

[75] Inventors: Michael Hanack, Tübingen; Gunter Hieber, Schorndorf-Oberberken, both of Fed. Rep. of Germany

[73] Assignee: Wacker-Chemie GmbH, Munich, Fed. Rep. of Germany

[21] Appl. No.: 628,960

[22] Filed: Dec. 17, 1990

[30] Foreign Application Priority Data

Feb. 22, 1990 [DE] Fed. Rep. of Germany ....... 4005648

[51] Int. Cl.$^5$ .................. C07D 209/56; C07D 409/06; C08F 28/06

[52] U.S. Cl. ...................................... 548/518; 549/53; 549/58; 549/59; 526/256

[58] Field of Search .................. 548/518, 430; 549/67, 549/59, 53, 58

[56] References Cited

U.S. PATENT DOCUMENTS 4,729,851 3/1988 Bräunling et al. .................. 252/500

FOREIGN PATENT DOCUMENTS 1017274 1/1966 United Kingdom .

OTHER PUBLICATIONS

A. Ulman and J. Manassen, "Symmetrically and Unsymmetrically Substituted Tetraphenyl-21, 23-Dithiaporphyrins", J. of the Chemical Society, Perkin I, pp. 1066–1069, 1979.

*Primary Examiner*—Joseph L. Schofer
*Assistant Examiner*—Wu C. Cheng

[57] ABSTRACT

The present invention relates to compounds of formula (I):

$$A-\underset{R'}{\overset{|}{C}}=B=\underset{R''}{\overset{|}{C}}-A, \qquad (I)$$

in which A represents the same or different heteroaryl radicals and substituted heteroaryl radicals; B represents dihydroheteroarenediylidene radicals or substituted dihydroheteroarenediylidene radicals or radicals obtainable from these radicals by oxidation on at least one hetero atom; and R' and R'' represent the same or different radicals, in particular hydrogen atoms, $C_1$- to $C_4$-alkyl radicals or radicals A, or cyano radicals, halogen atoms, radicals of the formula —COOR, or —OR, wherein R is a $C_1$- to $C_4$-alkyl radical, processes for preparing the same and polymers prepared therefrom.

9 Claims, No Drawings

HETEROARYLENEMETHINES AND POLYMERS PREPARED THEREFROM

The present invention relates to heteroarylenemethines, processes for their preparation and polymers prepared therefrom.

BACKGROUND OF THE INVENTION

Heteroarylenemethines are known in the art and poly(hetero)arylenemethines have been prepared by reacting trichloromethylfurfural or α,α,α,α'-pentachloro-p-xylene with (hetero)aromatics. (See U.S. Pat. No. 4,729,851 Bräunling et al, Wacker-Chemie GmbH). Heteroarylenemethines consisting of three heterocyclic rings connected by methine bridges substituted by in each case optionally substituted phenyl radicals are known from A.O. Patil and F. Wudl (Macromolecules 21, pages 540–542, 1988) and A. Ulman and J. Manassen (Journal of the Chemical Society, Perkin I, pages 1066–1069, 1979).

Therefore, it is an object of the present invention to provide novel starting materials for polymers, and in particular, for conductive polymers. Another object of the present invention is to provide novel polymers. A further object of the present invention is to provide novel processes for preparing starting materials for polymers.

SUMMARY OF THE INVENTION

The foregoing objects and others which will become apparent from the following description are accomplished in accordance with this invention, generally speaking, by providing compounds of the formula:

$$A-\underset{R'}{\underset{|}{C}}=B=\underset{R''}{\underset{|}{C}}-A, \qquad (I)$$

in which A represents the same or different heteroaryl radicals and substituted heteroaryl radicals; B represents dihydroheteroarenediylidene radicals or substituted dihydroheteroarenediylidene radicals or radicals obtainable from these radicals by oxidation of at least one hetero atom; and R' and R'' represent the same or different radicals, in particular hydrogen atoms, $C_1$- to $C_4$-alkyl radicals or radicals A, or cyano radicals, halogen atoms, radicals of the formula —COOR, or —OR, wherein R is a $C_1$- to $C_4$-alkyl radical.

DETAILED DESCRIPTION OF THE INVENTION

The radicals R' and R' are preferably the same or different radicals, in particular hydrogen atoms, $C_1$- to $C_4$-alkyl radicals or radicals A.

The radicals A are preferably optionally substituted, optionally benzo-fused heteroaryl radicals having five-membered rings. The radicals B are preferably optionally substituted, optionally benzo-fused dihydroheteroarenediylidene radicals having five-membered rings or the corresponding N-oxides, sulfoxides and/or sulfones. Preferred substituents for the radicals A and B are halogen atoms and optionally halogenated $C_1$- to $C_4$-alkyl radicals, in particular fluorine, chlorine and bromine atoms. It is preferred that radicals R' and R'' be hydrogen atoms or methyl groups or be the same as the radicals A. It is particularly preferred that radicals R' and R'' be the same, and more particularly for each of them to be hydrogen atoms or identical radicals A.

Examples of unsubstituted, optionally benzo-fused heteroaryl radicals A having five-membered rings are thiophenyl, benzothiophenyl, furanyl, benzofuranyl, pyrrolyl, indolyl, thiazolyl, thianaphthenyl, pyrazolyl, benzopyrazolyl, imidazolyl, benzimidazolyl, oxazolyl, benzoxazolyl, triazolyl and benzotriazolyl radicals.

Examples of unsubstituted, optionally benzo-fused dihydroheteroarenediylidene radicals B having five-membered rings and the radicals B obtainable from these radicals by oxidation of at least one hetero atom are dihydrothiophenediylidene radicals, such as the dihydrothiophene-2,5-diylidene radical, and the sulfoxide thereof, dihydrobenzothiophenediylidene radicals and sulfoxides thereof, 3-sulfolenediylidene, benzosulfolenediylidene, dihydropyrrol-2,5-diylidene, dihydroindole-2,3-diylidene, isoindoline-1,3-diylidene and dihydrofurandiylidene radicals, dihydrobenzofurandiylidene radicals, dihydroimidazolediylidene radicals, dihydrobenzimidazolediylidene radicals, dihydrooxazolediylidene radicals, dihydrobenzoxazolediylidene radicals, dihydrotriazolediylidene radicals and dihydrobenzotriazolediylidene radicals.

However, those radicals which are used with more than one benzene ring are also to be regarded as unsubstituted, optionally benzo-fused dihydroheteroarenediylidene radicals B having five-membered rings and the radicals B obtainable from these radicals by oxidation of at least one hetero atom. These are, for example, radicals of the formula (XXIII).

(XXIII)

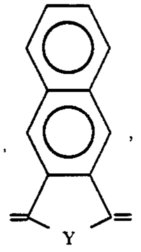

and those of the formula (XXIV):

(XXIV)

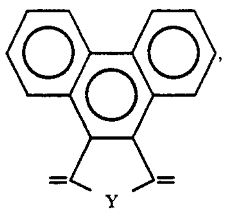

wherein, in the above formulas (XXIII) and (XXIV), Y is an oxygen or sulfur atom or a radical of the formula SO, $SO_2$, N-H, N-O or N-R, in which R represents a $C_1$- to $C_4$-alkyl radical.

Preferred radicals B are those having only one hetero atom in the ring. Preferred benzo-fused radicals B are the corresponding benzo[c]-heterocyclic radicals having five-membered rings and one hetero atom in the ring, that is radicals B in which the benzo-fusion is in the 3,4-position relative to the hetero atom (=position 1).

Other examples of preferred unsubstituted benzofused radicals B are radicals of the formula (II):

(II)

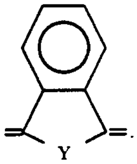

Examples of preferred unsubstituted radicals B which are not benzo-fused are radicals of the formula (III):

(III)

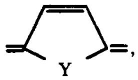

in which, in the abovementioned formulas (II) and (III), the radical Y is an oxygen or sulfur atom or a radical of the formula SO, $SO_2$, N-H, N-O or N-R, in which R represents a $C_1$- to $C_4$-alkyl radical. Preferred substituents of the radicals A and B are halogen atoms, psuedohalogen radicals, such as the cyano radical, optionally halogenated $C_1$-to $C_6$-hydrocarbon radicals and optionally halogenated $C_1$ to $C_6$-hydrocarbonoxy radicals.

Examples of substituents of the radicals A and B are fluorine, chlorine, bromine and iodine atoms, cyano radicals and methyl, ethyl, n-propyl, isopropyl, n-butyl, sec-butyl, t-butyl, chloromethyl, trichloromethyl, trifluoromethyl and 3,3,3-trifluoropropyl groups.

Examples of particularly preferred compounds of the formula (I) are those of the formula (IV), (V) or (VI):

(IV)

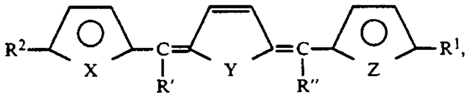

(V)

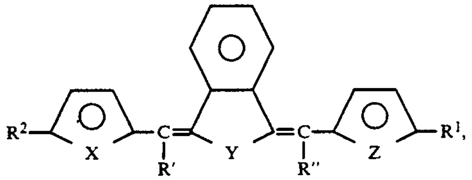

or (VI)

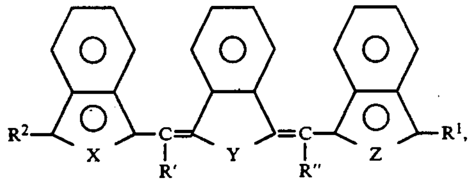

in which X and Z represent the same or different divalent radicals, in particular oxygen or sulfur atoms, or radicals of the formula N-H or N-R, $R^1$ and $R^2$ represent hydrogen atoms, halogen atoms, pseudo-halogen radicals, such as the cyano radical, optionally halogenated $C_1$ - to $C_6$-hydrocarbon radicals or optionally halogenated $C_1$- to $C_6$-hydrocarbonoxy radicals; Y and R are the same as in formulas (II) and (III); and R' and R'' are the same as in formula (I).

Of the abovementioned compounds of formulas (IV), (V) and (VI), those of formulas (IV) and (V) are particularly preferred.

Advantages of the sulfones of this invention (Y=-$SO_2$) are their high heat stability (200° C. to 250° C.) and their stability toward oxygen.

Processes

All the substances which can be used as reagents, additives, solvents, catalysts, doping agents, protective gases, polymers, other monomers and all the other substances which can be used in process 1, process 2 and processes for the preparation and processing of polymers, which processes are described below, can be employed individually or in a mixture:

Process 1:

The compounds of formula (I) can be prepared by reacting dihydroheteroarenes of formula (VII)

$BH_4$ (VII), with compounds of formulas (VIII) and (IX)

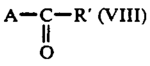 (VIII) and 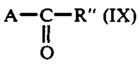 (IX)

in which, in the above formulas (VII), (VIII) and (IX), A, B, R' and R'' are the same as those in formula (I).

In each case one compound of formulas (VII), (VIII) and (IX) can be employed, and mixtures of at least two compounds of formula (VII), at least two compounds of formula (VIII) and/or at least two compounds of formula (IX) can also be employed.

Compounds of formula (I) in which R' and R'' are the same and in particular represent hydrogen atoms or the same radicals A, and especially hydrogen atoms, are preferably prepared by the process described above.

Compounds of formula (VII) which are preferably employed are those of formula (X)

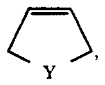 (X)

and/or compounds of formula (XI)

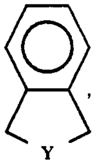 (XI)

and/or compounds of the formula (XXVII)

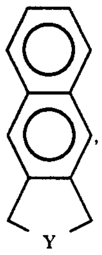 (XXVII)

and/or compounds of the formula (XXVIII)

(XXVIII)

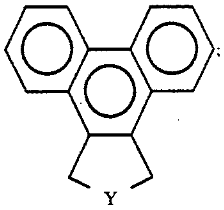

in which Y in each case is the same as in formula (II).

One compound of formula (X), (XI), (XXVII) or (XXVIII) can be employed in the process of this invention, and it is also possible to employ a mixture of compounds of formula (X), of compounds of formula (XI) or of at least one compound of formula (X) and at least one compound of formula (XI). Preferably, only one compound is employed, that is to say a compound of formula (X) or a compound of formula (XI).

Compounds of formulas (XII) or (XIII) are preferably employed as compounds of formula (VIII) in the process of this invention. Compounds of formula (IX) which are preferably employed in the process of this invention are compounds of formulas (XIV) or (XV):

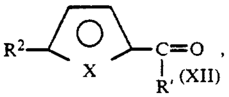 (XII) , 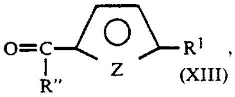 (XIII) ,

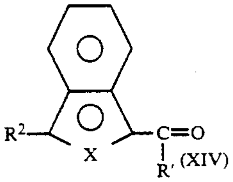 (XIV) or 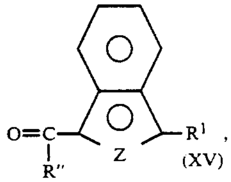 (XV) , in which $R^1$, $R^2$, R', R'', X and Z are the same as in formulas (IV) to (VI).

If Y in the product of formulas (IV), (V) or (VI) represents a sulfur atom, in a preferred embodiment of the process of this invention, compounds of formula (X) and/or (XI) in which Y represents a radical of the formula SO are employed and the sulfoxide obtained as the reaction product is then reduced.

It may be advantageous for one component to be employed in an excess or in less than the equivalent amount, either to accelerate the reaction or to suppress possible side reactions. However, compounds of formula (VII) are preferably employed in the process of this invention in a molar ratio to the sum of the compounds of the formulas (VIII) and (IX) of 0.1:1 to 10:1, and in particular, 0.3:1 to 0.75:1, and more particularly 0.4:1 to 0.6:1.

The process of this invention is preferably carried out in the presence of a base, in particular a strong base. Preferred bases are inter alia, alkali metal hydroxides and alkaline earth metal hydroxides, such as LiOH, NaOH, KOH, RbOH, CsOH, $Mg(OH)_2$, $Ca(OH)_2$, $Sr(OH)_2$ or $Ba(OH)_2$; alkali metal alcoholates and alkaline earth metal alcoholates, in particular the sodium and potassium salts of $C_1$ to $C_{18}$-alkanols, such as sodium methylate, sodium ethylate, potassium ethylate and sodium isopropylate; alkali metal amides and alkaline earth metal amides, in particular those of ammonia or of alkyl- and dialkylamines having in each case 1 to 18 carbon atoms per alkyl radical, such as $LiNH_2$, $NaNH_2$, $KNH_2$, lithium dimethylamide, lithium diethylamide and lithium diisopropylamide; alkali metal hydrides and alkaline earth metal hydrides, such as NaH, KH and $CaH_2$; alkali metal-alkyls and alkali earth metal alkyls, such as n-butyllithium and t-butyllithium; and amines, such as mono- and dialkylamines, pyridines, pyrimidines and morpholines.

The base, if employed, is preferably used in the process of this invention in amounts of from 5 mol percent to 1,000 mol percent, preferably from 10 mol percent to 100 mol percent, based on the sum of the number of moles employed of the compound of formulas (VIII) and (IX).

The process of this invention is preferably carried out at temperatures from 0° C. to 250° C., and in particular from 15° C. to 50° C.

The process of this invention can be carried out under pressures which far exceed or are far below 0.1 mPa (absolute); however, pressures of from 0.09 to 0.11 mPa (absolute), and in particular the pressure of the surrounding atmosphere, that is to say about 0.101 mPa (absolute) are preferred.

The process of this invention can be carried out in the presence or in the absence of solvents. It is preferably carried out in the presence of solvents. If solvents are used, solvents or solvent mixtures having a boiling point or boiling range of up to 120° C. under 0.1 mPa are preferred. Examples of such solvents are water; alcohols, such as methanol, ethanol, n-propanol and isopropanol; ethers, such as dioxane, tetrahydrofuran, diethyl ether and diethylene glycol dimethyl ether; chlorinated hydrocarbons, such as methylene chloride, chloroform, carbon tetrachloride, 1,2-dichloroethane and trichloroethylene; hydrocarbons, such as pentane, n-hexane isomer mixtures, heptane, octane, wash benzine, petroleum ether, benzene, toluene and xylenes; carbon disulfide and nitrobenzene, or mixtures of these solvents. Ketones, such as acetone, methyl ethyl ketone and methyl isobutyl ketone, are less preferred as solvents since ketones can form condensation products with compounds of formula (VII).

The term solvent does not mean that all the reaction components have to dissolve in the solvent. The reaction can also be carried out in a suspension or emulsion of one or more reaction components. The reaction can also be carried out in a solvent mixture having a miscibility gap, at least one reaction component being soluble in each of the mixed phases.

After the reaction, the base, if used, or reaction products thereof and the solvent, if used, are preferably removed. Bases and reaction products thereof can be removed, for example, by chromatography on inorganic adsorbents, such as silica gel or aluminum oxide, or in an ion exchanger. The reaction mixture is preferably freed from the solvent, if used, by distillation. In particular, the reaction mixture containing the products of this invention is purified by filtration over silica gel and subsequent removal of the solvent (if used) by distillation. The products are in general crystalline and can be further purified by recrystallization if a product of high purity is desired.

If Y in the product of formulas (IV), (V) or (VI) represents a sulfur atom, in a preferred embodiment of the process of this invention, compounds of formula (X) and/or (XI) in which Y represents a radical of the formula SO are employed and the sulfoxide obtained as the reaction product is then reduced. An analogous reaction is described by D. W. Chasar and T. M. Pratt (Synthesis 1976, page 262 . Particularly suitable reducing agents for this are $LiAlH_4$, HI, $NaBH_4$, $TiCl_2$, $PCl_3$, tributyl stannane, $H_2/Pd$, triphenylphosphine, stannane, acetyl chloride, $CH_3SiCl_3.NaI$, t-butyl bromide, tris(-dimethylamino)posphine.$I_2$ and 2-chloro-1,3,2-benzodioxaphosphole.

Process 2:

Compounds of formula (I) can also be prepared by reacting compounds (VIII) and/or (IX) with lithium salts of the heteroarenes corresponding to the radicals B in formula (I) (lithium compound for short) and then reducing the resultant products, preferably reacting them with hydrogen iodide and/or salts thereof, and in particular with hydrogen iodide. However, the reduction also proceeds, inter alia, with HCOOH, with other iodine reagents, such as $MgI_2/Mg$, with trialkyliodosilane or with a complex of trialkylchlorosilane and alkali metal iodide. In the reaction with iodine reagents, the hydroxyl groups of the biscarbinol primarily formed are in general replaced by iodine, after which iodine splits off —usually spontaneously. If desired, the iodine can be scavenged by suitable reagents, such as sodium dithionite.

This process is particularly recommended if R' and R" in the desired product of formula (I) in each case represents radicals A, that is optionally substituted heteroaryl radicals. Process 2 of this invention is preferably carried out at temperatures of from 0° C. to 100° C., and in particular from 15° C. to 50° C.

Process 2 of this invention can be carried out under pressures which far exceed or are far below 0.1 mPa (absolute); however, pressures of 0.09 to 0.11 mPa (absolute), in particular the pressure of the surrounding atmosphere, that is about 0.101 mPa (absolute), are preferred.

Process 2 of this invention can be carried out in the presence or absence of solvents. It is preferably carried out in the presence of solvents. If solvents are used, solvents or solvent mixtures having a boiling point or boiling range of up to 120° C. under 0.1 mPa are preferred. Examples of such solvents are the solvents and solvent mixtures mentioned for process 1.

It may be advantageous to employ one component in excess or in less than the equivalent amount, either to accelerate the reaction or to suppress possible side reactions. However, the lithium compound is preferably employed in process 2 of this invention in a molar ratio to the sum of the compounds of formulas (VIII) and (IX) of 0.1:1 to 10:1, and in particular 0.3:1 to 0.75:1, and more particularly 0.4:1 to 0.6:1.

In process 2 of this invention, the corresponding biscarbinol is primarily formed and is reacted, for example with hydrogen iodide or salts thereof to give the bis-iodine compound, which in turn spontaneously splits off iodine. This iodine which forms is preferably scavenged in process 2 by a reducing agent, for example, sodium dithionite.

The lithium salts of the heteroarenes corresponding to the radicals B in formula (I) which are preferably employed are the corresponding dilithium salts, in particular those of the formulas (XVI), (XVII), (XXV) and (XXVI):

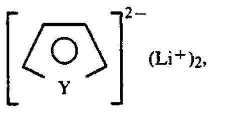
(XVI)

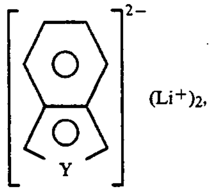
(XVII)

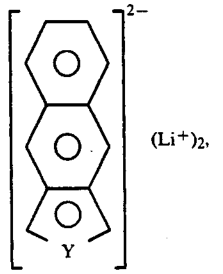
(XVII)

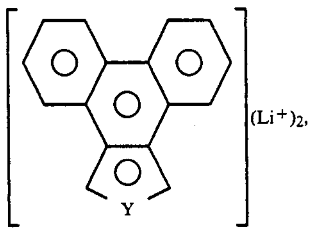
(XXVI)

in which Y is the same as above under formula (II).

Compounds of formulas (VIII) and/or (IX) which are employed in process 2 according to this invention are preferably those of formula (XVIII)

$A_2C{=}O$ (XVIII)

in which the radicals A are the same as those in formula (I), and in particular are identical radicals.

Polymers

The compounds of formula (I) are suitable for the preparation of polymers, in particular for the preparation of polymers having conjugated double bonds.

These are, in particular, polymers of formula (XIX):

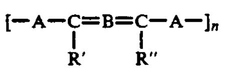
(XIX)

in which n is an integer and A, B, R' and R" are the same as those in formula (I).

These are preferably polymers of formulas (XX), (XXI), and (XXII):

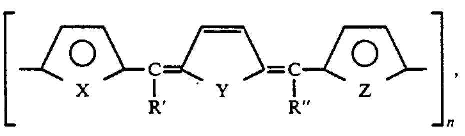
(XX)

-continued (XXI)

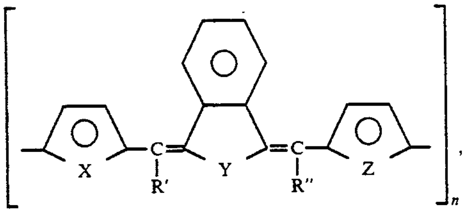

(XXII)

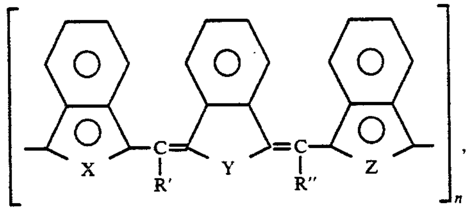

in which X and Z represent the same or different divalent radicals, in particular oxygen or sulfur atoms, or radicals of the formula N-H or N-R; n is the same as in formula (XIX); Y and R are the same as in formulas (II) and (III); and R' and R" are the same as in formula (I).

The radicals R' and R" should not result in too much steric hindrance, so that they interfere with conjugation in the polymer.

The radicals R' and R" are preferably in each case hydrogen atoms.

The number n is preferably at least 10, and more preferably at least 50.

The present invention also relates to complexes of polymers of formulas (XIX), (XX), (XXI) and (XXII) with doping agents. These complexes can be electrically charged.

The polymers of formulas (XIX), (XX), (XXI) and (XXII) can be prepared by known chemical and electrochemical treatment of the compounds of formulas (I), (IV), (V) and (VI).

The chemical polymerization can be carried out in the presence of many known oxidizing agents, for example by reaction with nitrosyl tetrafluoroborate, in particular for compounds of formulas (IV), (V) or (VI), in which $R_1$ and $R_2$ in each case represent hydrogen atoms. Compounds of formulas (IV), (V) or (VI) in which $R^1$ and $R^2$ in each case represent halogen atoms, in particular chlorine and/or bromine atoms, can be polymerized, inter alia, using organometallic compounds, and in particular n-butyllithium. The electrochemical polymerization is preferably carried out in the presence of a conductive salt or doping agent.

Examples of doping agents which can be added to the polymers of this invention are alkali metals, such as sodium or potassium; proton acids, such as $H_2SO_4$, $HClO_4$, $H_2Cr_2O_7$, HI and $HNO_3$; Lewis acids, such as $SbCl_5$, $AsCl_5$, $TiCl_4$, $FeCl_3$, $SnCl_4$, $ZnCl_2$ and $AsF_5$, and halogen, such as for example, iodine. It is possible to use one doping agent; however, at least two doping agents can be used as a mixture or successively with respect to time. The doped polymers preferably contain 0 to 50, preferably from 0.01 to 30 and more preferably from 0.1 to 20 percent by weight of doping agent.

If used, the doping agent or agents can be added before, during and/or after the polymerization. If doping is carried out after the polymerization, doping agents are preferably introduced by allowing the vapors or solutions of the doping agent to act on the polymers. The process is usually carried out at about 10° to 30° C., usually with exclusion of moisture and often with exclusion of air.

The polymerization is preferably carried out in the presence of a solvent or a solvent mixture. Preferred solvents or solvent mixtures are the solvents, individually or as a mixture, listed as preferred for process 1. Depending on the reagents used for the polymerization, it may be advisable to use anhydrous or aprotic solvents. If appropriate, it may be advantageous to carry out the polymerization under a protective gas, such as nitrogen or argon.

It may be advantageous to carry out the polymerization of this invention in the presence of at least one other monomer or the corresponding polymer or polymers. The compound of formula (I) and at least one other monomer can be polymerized simultaneously or in succession in any desired sequence. Polymerization of at least one compound of formula (I) in a matrix of finely divided polymer, in a solution of polymer and/or in a matrix of polymer swollen in solvent is particularly preferred. Such a process is described in DE-A-3,829,753 (application date Sep. 1, 1988, R. Becker et al, Wacker-Chemie GmbH) and in the U.S. application of the same priority date (Ser. No. 397,590, application date Aug. 23, 1989). Such modified polymers can be shaped and processed without difficulty, especially if the other polymer is a thermoplastic.

Examples of such suitable other polymers are organic synthetic polymers, such as polyvinyl chloride, polyethylene, polypropylene, polyvinyl acetate, polycarbonate, polyacrylate, polymethacrylate, polymethyl methacrylate, polystyrene, polyacrylonitrile, polyvinylidene chloride, polyvinyl fluoride, polyvinylidene fluoride, polyvinylidene cyanide, polybutadiene, polyisoprene, polyether, polyester, polyamide, polyimide, silicones, polyvinyl alcohol, polyvinylpyrrolidone, polyacrylamide, polyethylene glycol and derivatives thereof and the like, including copolymers, such as styrene/acrylate copolymers, vinyl acetate/acrylate copolymers and ethylene/vinyl acetate copolymers, as well as naturally occurring polymers, such as cellulose, starch, casein and naturally occurring rubber, and also semisynthetic high molecular weight compounds, such as cellulose derivatives, for example methylcellulose, hydroxymethylcellulose and carboxymethylcellulose.

Examples of other monomers which are suitable are the monomers and monomer mixtures corresponding to the polymers mentioned above.

The polymers of this invention are electrically conductive or semiconductive compounds, depending on the nature and extent of their doping. They can be employed, for example, in batteries, accumulators, circuits, switches and electrodes, as or in electrical shields and electrochemical sensors, or as antistatic materials, inter alia for clothing or for electrical and electronic equipment. They are also suitable for coatings on optical articles, such as lenses, panes, inter alia window panes, inter alia for thermoinsulation thereof. They can also be used in preparations containing an active substance, in particular in the field of agriculture and medicine; controlled release of active substances, such as plant protection agents, pest control agents and medicaments, can in this way take place. The release of the active substance, for example, from an implant on or in the human or animal body, can be regulated by the application of a control voltage. If appropriate, the polymers of this invention can be employed as a mixture with other polymers. Depending on their ability to undergo complexing, they can be employed as absorbents for chemicals, inter alia for heavy metals or salts thereof. They can be used as catalysts or a constituent or precursor thereof, for example, if they are complexed with a catalytically active metal salt.

On the basis of their complexing properties, the polymers of this invention can be used as absorbents for heavy metals and as catalysts.

In the following examples:

(a) all amounts are by weight;
(b) all pressures are 0.10 mPa (absolute);
(c) all temperatures are 20° C.;
(d) all UV spectra are measured in methanol, the main absorption bands being shown in bold and the wavelengths being given in nm;
(e) all $^1$H-NMR spectra are measured in dimethyl sulfoxide-$d_6$ using tetramethylsilane (TMS) as the internal standard; the chemical shifts are stated in ppm relative to TMS;
(f) all starting substances are commercially available or can be prepared by processes described in the literature;
(g) all products are worked up with the aid of flash chromatography, with the exception of the polymers.

EXAMPLES

Example 1: Sulfones

1.1

2,5-Bis-(2-thienylmethylidene)-2,5-dihydrothiophene-1,1-dioxide (1a) ($C_{14}H_{10}O_2S_3$, MW=306)

About 80 mmol (9.4 g) of 3-sulfolene (MW=118) and 170 mmol (19.04 g) (15.9 ml) of thiophene-2-aldehyde (MW=112, d=1.2 g/cm$^3$) were added to an alkaline solution of 1 g of NaOH in 200 ml of ethanol. The mixture was stirred at room temperature for 3 days. A yellow precipitate formed which was filtered off with suction and washed thoroughly with ethanol and water.

Crude Yield: 2.5 g

The reaction solution was concentrated, and acetone was added to the residue. Removal of the polymeric constituents by chromatography was performed using silica gel, and acetone as the eluent. The acetone solution was concentrated and the residue was placed in a refrigerator. Brown-yellow crystals were obtained.

Crude Yield: 1 g

The crude product was recrystallized twice from acetone. Orange-yellow needles were obtained.

Yield: 2 g =8.7 percent of theory.
Melting point: 220° C.
MS: m/e 306 (M+).

1.2

2,5-Bis-(2-N-methylpyrryl)-methylidene-2,5-dihydrothiophene-1,1-dioxide (1b) $C_{16}H_{16}N_2O_2S$, MW=300)

About 30 mmol (3.56 g) of 3-sulfolene (MW=118) and 80 mmol (8.72 g) (8.6 ml) of N-methylpyrrole-2-aldehyde (MW=109, d=1.016 g/cm$^3$) were added to 100 ml of a solution, saturated in the cold, of $NaOCH_3$ in methanol. After the mixture had been boiled under reflux for 4 days, the precipitate formed was filtered off with suction and washed with methanol and water.

Crude Yield: 8 g

Recrystallization twice from acetone gave deep red crystals.

Yield: 4 g=44.4 percent theory.
Melting point: 243° C.
MS: m/e 300 (M+).

1.3

2,5-Bis-(2-pyrrylmethylidene)-2,5-dihydrothiophene-1,1-dioxide (1c) ($C_{14}H_{12}N_2O_2S$, MW=272)

About 20 mmol (2.36 g) of 3-sulfolene (MW=118) and 42 mmol (4 g) of pyrrole-2-aldehyde (MW=95) were dissolved in an alkaline solution of 1.5 g of NaOH and 1.9 g of $NaOCH_3$ in 70 ml of methanol. The mixture was stirred at room temperature for 5 days. The black-brown reaction mixture was concentrated.

The purification by chromatography was performed using silica gel/ether, silica gel/toluene:ether=2:3 and finally using aluminum oxide/ether. When the ethereal solution was concentrated, a yellow precipitate was obtained, which was filtered off with suction and dried.

Yield: 80 mg=1.5 percent theory.
Melting point: 174° C. (decomposition).
MS: m/e 272 (M+).

1.4

2,5-Bis-[2-(5-bromothienyl)methylidene]-2,5-didhydrothiophene-1,1-dioxide (1d) $C_{14}H_8Br_2O_2S_3$, MW=463.8)

About 10 mmol (1.18 g) of 3-sulfolene (MW=118) and 22 mmol (4.2 g) (2.6 ml) of 5-bromothiophene-2-aldehyde (MW=190.9, d=1.607 g/cm$^3$) were added to a solution of 0.6 g of NaOH in 25 ml of $H_2O$ and 10 ml of tetrahydrofuran. During this procedure, the aldehyde only partly dissolved; two phases were obtained. After the mixture had been stirred at room temperature for 3 days, the yellow precipitate formed was filtered off with suction.

Crude Product: 300 mg

The reaction mixture was concentrated and ethyl acetate was added to the residue. Purification by chromatography was performed first using silica gel/ethyl acetate and then using $Al_2O_3$/toluene or silica gel/toluene. The toluene solution was concentrated and the residue was placed in a refrigerator. Yellow crystals were obtained.

Crude Product: 500 mg

Recrystallization twice from acetone gave yellow crystals.

Yield: 500 mg=10.8 percent of theory.
Melting point: 249°-50° C.
MS: m/e 462 (M+).

1.5

1,3-Bis-(arylmethylidene)-1,3-dihydroisothianaphthene-2,2-dioxide (3)

About 10 mmol (1.68 g) of 1,3-dihydroisothianaphthene-2,2-dioxide (MW=168) (2) and 22 mmol of aryl-2-aldehyde were added to 70 ml of a solution, saturated in the cold, of $NaOCH_3$ in methanol. After the mixture had been boiled under reflux for 3 days, a precipitate formed which was filtered off with suction and washed with a large quantity of methanol. It was recrystallized from acetone. aryl=2-thienyl (3a) ($C_{18}H_{12}O_2S_3$, MW=356) yellow crystals Yield: 600 mg=16.9 percent of theory.
Melting point: 223° C.
MS: m/e 356 (M+).

aryl=2-(N-methylpyrryl) (3b) ($C_{20}H_{18}N_2O_2S$, MW=350) yellow needle-shaped crystals Yield: 1.5 g=42.8 percent of theory.
Melting point: 298° C.

MS: m/e 350 ($M^+$).

aryl=2-pyrryl (3c) ($C_{18}H_{14}N_2O_2S$, MW=322)

The synthesis was performed analogously. After purification by chromatography using silica gel/ethyl acetate and silica gel/toluene, the product crystallized from toluene in the form of yellow crystals.

Yield: 1.1 g=34.2 percent theory.

Melting point: 228° C. (decomposition).

MS: m/e 322 ($M^+$).

The UV and NMR spectral data are given in Table 1 and Table 2, respectively.

TABLE 1

| UV absorption in (nm) | | | | | | |
|---|---|---|---|---|---|---|
| 1a | 416 sh | 392.4 | 355 | 323 | 265.6 | |
| 1b | 430 | | | 343 | 285 | 211 |
| 1c | 418 | | 369 | 337 | 280 | 217 |
| 1d | 429 sh | 408 | 388 sh | 330 | 276 | 209 |
| 3a | 368 | 357 sh | 335 | 323 sh | 244 | 209 sh |
| 3b | 396 | 355 | | 266 | 236 sh | 211 |
| 3c | 387 | 345 | | 266 | 236 | 210 |

TABLE 2

$^1H$-NMR data (in DMSO-$d_6$)

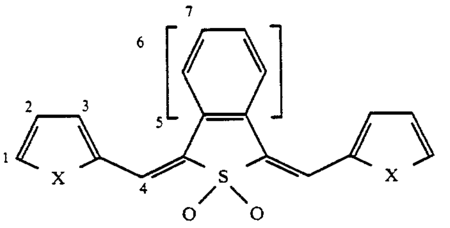

| | H 1 | H 2 | H 3 | H 4 | H 5 | H 6 | H 7 |
|---|---|---|---|---|---|---|---|
| 1a | 7.91 d | 7.28 dd | 7.67 d | 7.49 s | 7.46 s | | |
| 1b[a] | 7.1 dd | 6.23 dd | 6.83 dd | 6.89 s | 7.35 s | | |
| 1c[b] | 7.1 dd | 6.30 dd | 6.77 dd | 6.86 s | 7.35 s | | |
| 1d | | 7.38 d | 7.51 d | 7.44 s | 7.39 s | | |
| 3a[c] | 7.90 d | 7.25 dd | 7.87 d | 8.05 s | | 7.91 dd | 7.48 dd |
| 3b[d] | 7.09 dd | 6.20 dd | 7.34 dd | 7.47 s | | 7.86 dd | 7.36 dd |
| 3c[e] | 7.17 d | 6.31 dd | 7.17 d | 7.51 s | | 7.60 dd | 7.36 dd |

[a] $N-CH_3$ = 3.75 ppm
[b] N—H = 11.21 ppm (acetone-$d_6$)
[c] heavily overlapping multiplets as H1, H3 and H5
[d] $N-CH_3$ = 3.82 ppm
[e] N—H = 11.21 ppm
s = singlet
d = doublet
dd = doublet of a doublet all data in ppm EXAMPLE 2: Sulfoxides 2.1

2,5-(Bis-(2-thienylmethylidene)-2,5-dihydrothiophene 1-oxide (5) ($C_{14}H_{10}OS_3$, MW=290)

About 30 mmol (3.06 g) of 2,5-dihydrothiopnene-1-oxide (MW=102) (4) and 70 mmol=(7.84 g) (6.5ml) of thiophene-2-aldehyde (MW—112, d=1.2 g/cm$^3$) were added to a solution containing 0.9 g of NaOH in 50 ml of $H_2O$ and 12.5 ml of tetrahydrofuran. The mixture was stirred for 2 days. Purification was performed by separation by column chromatography; the reaction mixture was applied to a column of silica gel/diethyl ether. The aldehyde was eluted with ether; the product was eluted with ethyl acetate. When the solvent was stripped off in vacuo, the product precipitated. The precipitate was filtered off with suction and dried.

Yield: 500 mg=5.7 percent of theory.

Melting point: 136°-137° C. (decomposition).

MS: m/e 290 ($M^+$).

2.2

1,3-Bis-(arylmethylidene)-1,3-dihydroisothianaphthene 2-oxide (7)

About 12 mmol (1.82 g) of 1,3-dihydroisothianaphthene-2-oxide (MW=152) (6) and 26 mmol (2.9 g) (2.4 ml) of thiophene-2-aldehyde (MW=112, d=1.2 g/cm$^3$) were added to a solution containing 1 g of NaOH in 30 ml of methanol. The mixture was stirred at 40° C. for 3 days.

aryl=2-thienyl (7a) ($C_{18}H_{12}OS_3$, MW=340)

Working up: A precipitate which had separated out was filtered off with suction, washed with methanol and recrystallized from acetone.

Yield: 1.8 g=44 percent of theory.

Melting point: 195° C. (decomposition).

MS m/e 340 ($M^+$).

aryl=2-(N-methylpyrryl) (7b) ($C_{20}H_{18}N_2OS$, MW=334)

Working up: The reaction mixture was concentrated and the residue was chromatographed using silica gel/ether. The product was eluted with ethyl acetate. When the solvent was stripped off, the product was obtained in the form of violet crystals.

Yield: 500 mg=12.5 percent of theory.

Melting point: 233° C. (decomposition).

MS: m/e 334 ($M^+$).

The UV and NMR spectral data are given in Table 3 and Table 4, respectively.

TABLE 3

| UV absorption in (nm) | | | | | | |
|---|---|---|---|---|---|---|
| 5 | 412 sh | 392 | 328 | 277 | 224 sh | 212 |
| 7a | | 361 | 330 | 273 | | |
| 7b | | 390 | 354 | 273 | 240 | |

TABLE 4

$^1H$-NMR data

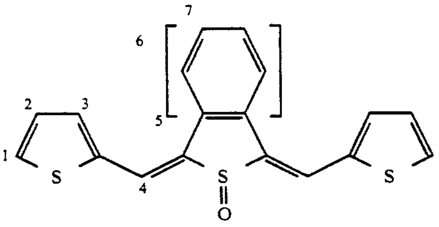

| | H 1 | H 2 | H 3 | H 4 | H 5 | H 6 | H 7 |
|---|---|---|---|---|---|---|---|
| 5 | 7.82 d | 7.20 dd | 7.53 d | 7.51 s | 7.4 s | | |
| 7a | 7.88 dd | 7.24 dd | 7.67 d | 8.18 s | | 7.89 dd | 7.43 dd |
| 7b[a] | 7.07 dd | 6.23 dd | 7.17 dd | 7.75 s | | 7.91 dd | 7.36 dd |

[a] $N-CH_3$ = 3.38 ppm
s = singlet,
d = doublet,
dd = doublet of a doublet all data in ppm EXAMPLE 3: "Sulfides"

3.1

2,5-Bis-(2-thienylmethylidene)-2,5-dihydrothiophene (9a) ($C_{14}H_{10}S_3$, MW=274)

About 1.1 mol (0.19 g) (0.13 ml) of 2-chloro-1,3,2-benzodioxaphosphole (MW=174.5, d=1.46 g/cm$^3$) is slowly added to a solution containing 1.03 mmol (300 mg) of 5a (MW=292) in 30 ml of dry toluene and 1.25 mmol (0.1 g) (0.1 ml) pyridine (MW=79, d=0.978 g/cm$^3$). The mixture is then stirred at room temperature for 2 to 3 hours. The reaction is carried out with exclusion of air and moisture. The reaction takes place almost quantitatively. The product is purified by column chromatography (silica gel/ether : n-hexane 1:1). After the solvent has been stripped off, a yellow powder which is relatively stable in air but must be stored in an $N_2$ atmosphere is obtained.

Yield: 220 mg=80.3 percent theory.

Melting point: 125°-130° C. (decomposed without a defined melting point).

MS: m/e 274 (M+)

3.2

1,3-Bis-(2-thienylmethylidene)-1,3-dihydroisothianaphthene (9b) ($C_{18}H_{12}S_3$, MW=324)

About 4 mmol=(0.7 g)=(0.5 ml) of 2-chloro-1,3,2-benzodioxaphosphole (MW=174.5, d=1.46 g/cm³) are slowly added to a solution containing 3 mmol (0.98 g) of methylidene)-1,3-dihydroisothianaphathene-2-oxide (7a) (MW=340) in 20 ml of dry toluene and 4 mmol (0.32 g) (0.33 ml) of pyridine (MW=79, d=0.978 g/cm³). The reaction is carried out and the product is worked up in accordance with 9a, Example 3.1.

Yield: 800 mg=82.3 percent of theory.

Melting point: 183° C.

MS: m/e 324 (M+).

3.3

2.5-Bis-(di-2-thienyl)-methylidene)-2,5-dihydrothiophene (9c) ($C_{22}H_{14}S_5$, MW=438)

A solution containing 10 g of $Na_2S_2O_4$ and 5 ml of concentrated hydriodic acid in 100 ml of $H_2O$ is added to a solution containing 6 mmol (2.8 g) of 2,5-bis-(di-2-thienyl)hydroxymethyl)-thiophene (MW=472) (8) in 100 ml of toluene. After the two-phase system has been stirred for 12 hours, the reaction mixture is neutralized with $NaHCO_3$ and extracted several times by shaking with ether. An orange-violet solution is obtained. The product is isolated by column chromatography (silica gel/n-hexane). The orange-red solution is evaporated on a rotary evaporator and the red solid is recrystallized from acetone.

Yield: 600 mg=23 percent of theory.

Melting point: 157° C.

MS: m/e 438 (M+).

The UV and NMR spectral data are given in Table 5 and Table 6, respectively.

TABLE 5

| | UV absorptions in (nm) | | | | | |
|---|---|---|---|---|---|---|
| 9a | 433 | 415 | 395 sh | 297 | 291 sh | 232 |
| 9b | 423 | 400 | 380 | 343 | 326 sh | 316 |
| | | | | 304 sh | 263 | 235 sh |
| 9c | 472 | 447 sh | 305 | 228 | | |

TABLE 6

¹H-NMR data

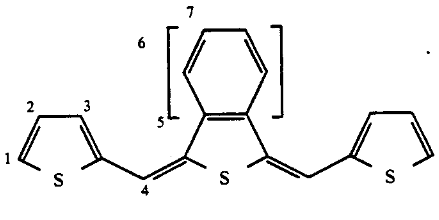

| | H 1 | H 2 | H 3 | H 4 | H 5 | H 6 | H 7 |
|---|---|---|---|---|---|---|---|
| 9a | 7.68 d | 7.17 dd | 7.26 d | 7.24 s | 7.0 s | | |
| 9b | 7.73 d | 7.21 dd | 7.38 d | 7.91 s | | 8.04 dd | 7.45 dd |

TABLE 6-continued

¹H-NMR data

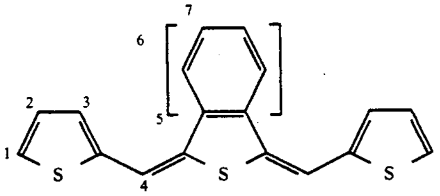

| | H 1 | H 2 | H 3 | H 4 | H 5 | H 6 | H 7 |
|---|---|---|---|---|---|---|---|
| 9c[a] | | 7.35 to 7.03 | | | 6.87 s | | |

[a]$CDCl_3$ = overlapping multiplets

Example 4: Polymers 4.1 The compounds (1a) and (1b) prepared according to Example 1.1 and 1.2 were polymerized using nitrosyl tetrafluoroborate in 1,2-dichloroethane as the solvent. Brown to black precipitates were obtained.

4.2 The compounds (1d) prepared according to Example 1.3 were polymerized using n-butyllithium in the presence of $CUCL_2$ in tetrahydrofuran. A brown precipitate was obtained.

4.3 The compounds (1a) and (1b) prepared according to Examples 1.1 and 1.2 were polymerized electrochemically in acetonitrile in the presence of tetra-n-butylammonium hexafluorophosphate as the conductive salt. A brown precipitate was obtained.

4.4 compound (9a) according to Example 3.1 was polymerized electrochemically in methylene chloride in the presence of $(n\text{-}C_4H_9)_4NBF_4$ as the conductive salt. A black-violet precipitate which had a broad UV absorption with a maximum at 900 nm was obtained on ITO (indium tin oxide)-glass as the electrode material: This could be an indication of a polymer having a band structure with a band gap of approximately 1.3 eV.

What is claimed is:

1. A process for preparing a compound of the formula

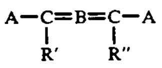

(I)

in which A is heteroaryl radicals having five membered rings selected from the group consisting of thiophenyl, benzothiophenyl, furanyl, benzofuranyl, pyrrolyl, indolyl, thiazolyl, thianaphthenyl, pyrazolyl, benzopyrazolyl, imidazolyl, benzimidazolyl, oxazolyl, benzoxazolyl, triazolyl and benzotriazolyl radicals and optionally heteroaryl radicals substituted with halogen atoms, cyano radicals, $C_1$- to $C_6$-hydrocarbon radicals, halogenated $C_1$- to $C_6$-hydrocarbon radicals, $C_1$- to $C_6$-hydrocarbonoxy radicals and halogenated $C_1$- to $C_6$-hydrocarbonoxy radicals; B is dihydroheteroarenediylidene radicals having five membered rings selected from the group consisting of dihydrothiophene-2,5-diylidene, dihydrobenzothiophenediylidene radicals and radicals of the formula (XXIII)

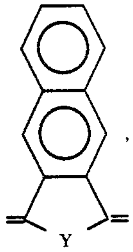

and those of the formula (XXIV)

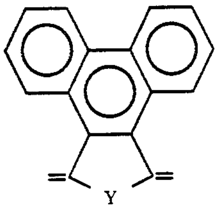

wherein Y is an oxygen or sulfur atom or a radical of the formula SO, $SO_2$, and optionally, dihydroheteroarenediylidene radicals substituted with halogen atoms, cyano radicals, $C_1$- to $C_6$-hydrocarbon radicals, halogenated $C_1$- to $C_6$-hydrocarbon radicals, $C_1$- to $C_6$-hydrocarbonoxy radicals and halogenated Chd 1- to $C_6$-hydrocarbonoxy radicals and the corresponding sulfoxides or sulfones of the radicals B, and R' and R'' are selected from the group consisting of hydrogen atoms, $C_1$- to $C_4$-alkyl radicals, radicals A, cyano radicals, halogen atoms, radicals of the formula —COOR, and —OR, in which R is a $C_1$- to $C_4$-alkyl radical and A is the same as above, which comprises reacting a dihydroheteroarene of the formula $BH_4$ (VII)

in which B is the same as above and in each case 2 hydrogen atoms are attached to one carbon atoms, with a compound of the formula

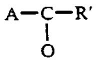

(VIII)

and a compound of the formula

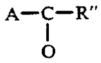

(IX)

in which A, R' and R'' are the same as above.

2. A process for preparing a compound selected from the group consisting of (IV)

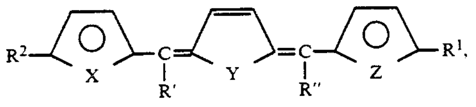

-continued (V)

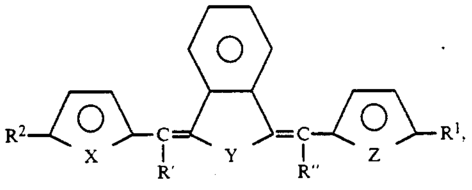

and (VI)

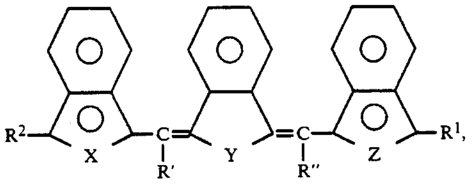

in which X and Z are divalent radicals selected from the group consisting of oxygen atoms, sulfur atoms, radicals of the formula N-H and N-R, R is a $C_1$- to $C_4$- alkyl radical; $R^1$ and $R^2$ are each selected from the group consisting of hydrogen atoms, halogen atoms, cyano radicals, $C_1$- to $C_6$-hydrocarbon radicals, halogenated $C_1$-to $C_6$-hydrocarbon radicals, $C_1$-to $C_6$-hydrocarbonoxy radicals and halogenated $C_1$- to $C_6$-hydrocarbonoxy radicals; Y is selected from the group consisting of an oxygen atom, a sulfur atom, and a radical selected from the group consisting of the formula SO, and $SO_2$; and R' and R'' are selected from the group consisting of hydrogen atoms, $C_1$- to $C_4$-alkyl radicals, radicals A, in which A is selected from the group consisting of thiophenyl, benzothiophenyl, furanyl, benzofuranyl, pyrrolyl, indolyl, thiazolyl, thianaphthenyl, pyrazolyl, benzopyrazolyl, imidazolyl, benzimidazolyl, oxazolyl, benzoxazolyl, triazolyl and benzotriazolyl radicals and optionally substituted with halogen atoms, cyano radicals, $C_1$- to $C_6$-hydrocarbon radicals, halogenated $C_1$- to $C_6$-hydrocarbon radicals, $C_1$- to $C_6$-hydrocarbonoxy radicals, halogenated $C_1$- to $C_6$-hydrocarbononoxy radicals; cyano radicals, halogen atoms, radicals of the formula —COOR, and —OR, in which R is the same as above, in which a compound selected from the group consisting of the formula (X)

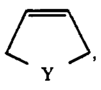

a compound of the formula (XI)

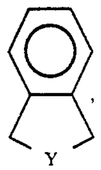

a compound of the formula (XXVII)

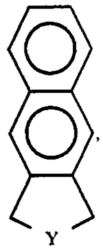

a compound of the formula (XXVIII)

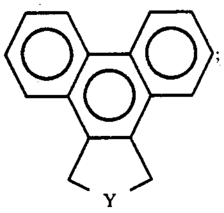

and mixtures thereof is reacted with a compound selected from the group consisting of the formulas

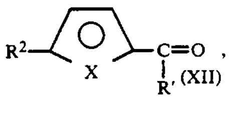 (XII), 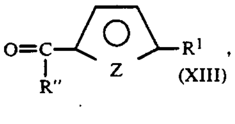 (XIII),

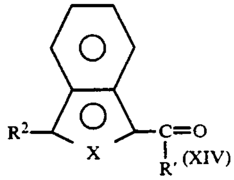 (XIV) or 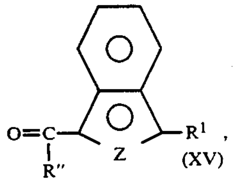 (XV), in which $R^1$, $R^2$, R', R'', X, Y and Z are the same as above, with the proviso that if Y in the product of formulas (IV), (V) or (VI) represents a sulfur atom, compounds of the formulas (X), (XI), (XXVII) and (XXVIII) in which Y represents a radical of the formula SO are employed, and the resultant sulfoxide thus obtained as the reaction product is then reduced.

3. The process of claim 1 in which R' and R'' are hydrogen atoms.

4. The process of claim 2, in which $R^1$ and $R^2$ are hydrogen atoms.

5. The process of claim 1, in which the reaction is carried out in the presence of a base.

6. The process of claim 2, in which the reaction is carried out in the presence of a base.

7. The process of claim 3, in which the reaction is carried out in the presence of a base.

8. A process for preparing 2,5-bis-(2-N-methylpyrryl)methylidene-2,5-dihydrothiophene-1,1-dioxide, which comprises reacting 3-sulfolene with N-methylpyrrole-2-aldehyde in the presence of a saturated sodium methoxide methanol solution and thereafter recovering the crystallized product.

9. A process for preparing a compound of the formula

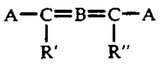 (I)

in which A is heteroaryl radicals having five membered rings selected from the group consisting of thiophenyl, benzothiophenyl, furanyl, benzofuranyl, pyrrolyl, indolyl, thiazolyl, thianaphthenyl, pyrazolyl, benzopyrazolyl, imidazolyl, benzimidazolyl, oxazolyl, benzoxazolyl, triazolyl and benzotriazolyl radicals and optionally heteroaryl radicals substituted with halogen atoms, cyano radicals, $C_1$- to $C_6$-hydrocarbon radicals, halogenated $C_1$- to $C_6$-hydrocarbon radicals, $C_1$- to $C_6$-hydrocarbonoxy radicals; B is dihydroheteroarenediylidene radicals having five membered rings selected from the group consisting of dihydrothiophene-2,5-diylidene, dihydrobenzothiophenediylidene radicals and radicals of the formula (XXIII)

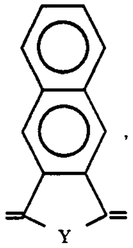

and those of the formula (XXIV)

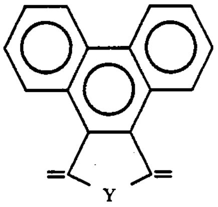

wherein Y is an oxygen or sulfur atom or a radical of the formula SO or $SO_2$, and optionally, dihydroheteroarenediylidene radicals substituted with halogen atoms, cyano radicals, $C_1$- to $C_6$-hydrocarbon radicals, halogenated $C_1$- to $C_6$-hydrocarbon radicals, $C_1$- to $C_6$-hydrocarbonoxy radicals and halogenated $C_1$- to $C_6$-hydrocarbonoxy radicals and the corresponding sulfoxides or sulfones of the radicals B, and R' and R'' are selected from the group consisting of hydrogen atoms, $C_1$- to $C_4$-alkyl radicals, radicals A, cyano radicals, halogen atoms, radicals of the formula —COOR, and —OR, in which R is a $C_1$- to $C_4$-alkyl radical and A is the same as above, which comprises reacting a compound of the formula

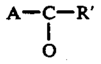 (VIII)

and a compound of the formula

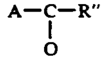 (IX)

in which A, R' and R'' are the same as above with a lithium salt of a heteroarene radical corresponding to the radicals B in formula I and thereafter reducing the resultant product with hydrogen iodide and/or salts thereof.

* * * * *

UNITED STATES PATENT AND TRADEMARK OFFICE
CERTIFICATE OF CORRECTION

PATENT NO. : 5,136,049

DATED : August 4, 1992

INVENTOR(S) : Dr. Michael Hanack and Gunter Hiever

It is certified that error appears in the above-identified patent and that said Letters Patent is hereby corrected as shown below:

In Claim 1, column 17, line 31 of the Patent, after "halogenated," delete "Chd 1-" and substitute --- $C_1$ ---, line 50, delete the formula "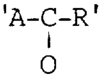" and substitute --- 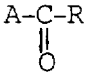 ---, line 55 delete the formula "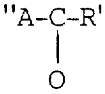" and substitute --- 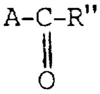 ---.

In Claim 9, column 20, line 14, after "radicals" insert --- and halogenated $C_1$- to $C_6$-hydrocarbonoxy radicals; ---, line 60, delete the formula "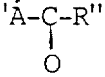" and substitute --- 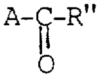 ---.

Signed and Sealed this

Fifth Day of October, 1993

Attest:

BRUCE LEHMAN

*Attesting Officer* *Commissioner of Patents and Trademarks*